United States Patent
Frank

(10) Patent No.: US 9,795,708 B1
(45) Date of Patent: Oct. 24, 2017

(54) METHOD FOR MACHINING METALLIC FOAM

(75) Inventor: Matthew C. Frank, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 2473 days.

(21) Appl. No.: 12/361,858

(22) Filed: Jan. 29, 2009

Related U.S. Application Data

(60) Provisional application No. 61/024,945, filed on Jan. 31, 2008.

(51) Int. Cl.
    *A61L 27/04*     (2006.01)
    *A61F 2/28*     (2006.01)
    *B23D 79/00*     (2006.01)
    *B23P 13/02*     (2006.01)

(52) U.S. Cl.
    CPC ............... *A61L 27/04* (2013.01); *A61F 2/28* (2013.01); *B23D 79/00* (2013.01); *B23P 13/02* (2013.01)

(58) Field of Classification Search
    USPC ........................................................... 29/557
    See application file for complete search history.

(56) References Cited

U.S. PATENT DOCUMENTS

| | | | |
|---|---|---|---|
| 6,159,378 A * | 12/2000 | Holman et al. | ............... 210/695 |
| 2003/0051333 A1* | 3/2003 | Trybus | ............................ 29/558 |
| 2003/0153981 A1 | 8/2003 | Wang et al. | |
| 2004/0089963 A1* | 5/2004 | Olari | ........................ B29C 35/16 264/28 |
| 2007/0106322 A1* | 5/2007 | Gilson et al. | .................. 606/200 |

OTHER PUBLICATIONS

The Use of a Drill Press for Boring Holes in Stoppers, W.B. Stengle, Journal of Chemical Education, 1951, 28(7), p. 393.*
Rahbek, O., et al., "Particle Migration and Gap Healing Around Trabecular Metal Implants", International Orthopaedics (SICOT) (2005) 29:368-374.
Wiley InterScience, "Journal of Biomedical Materials Research Part B:Applied Biomaterials", Jul. 12, 2006, http://www3.interscience.wiley.com/journal/112701507/abstract, retrieved on Jan. 29, 2009, 2 pages.
MD Medical Design, Gordon, Leslie, "Wire EDM for Tough Materials", Nov. 1, 2005, http://www.printthis.clickability.com/pt/cpt?action=cpt&title=Wire+EDM+for+Tough+M . . . , retrieved Jan. 29, 2009, 2 pages.

* cited by examiner

*Primary Examiner* — Moshe Wilensky
(74) *Attorney, Agent, or Firm* — McKee, Voorhees & Sease, PLC

(57) ABSTRACT

A method of cutting metallic foams that eliminates the problem of smeared surfaces is provided. The method involves infiltration of the foam with another material to serve as a support structure to the foam when being cut. The method can be executed using softer polymeric materials such as waxes, which are then frozen for machining. These materials are subsequently heated and removed from the foam. In a similar manner, epoxy material can be used, which requires no freezing. In this method, the epoxy material is burnt from the foam upon completion of machining. The method allows for machining foams using conventional machining processes, rather than non traditional methods such as electrical discharge machining.

17 Claims, 2 Drawing Sheets

METHOD FOR MACHINING METALLIC FOAM

CROSS-REFERENCE TO RELATED APPLICATIONS

This application claims priority under 35 U.S.C. §119(e) to provisional application Ser. No. 61/024,945 filed Jan. 31, 2008, herein incorporated by reference in its entirety.

FIELD OF THE INVENTION

The present invention relates to a process of cutting metallic foams that eliminates the problem of smeared surfaces.

BACKGROUND OF THE INVENTION

Metallic foams are metals that have porosity, and actually resemble foam or sponges. One particular metallic foam is called Trabecular metal, and is used as a material for bone implants. A foam material is useful in the body because the surrounding bone will grow into the cellular structure and the foam insert will generate a very strong bond with the natural bone. Trabecular metal is made of pure Tantalum metal. The problem with the material is that it cannot be cut using traditional machining methods. If the material is cut using traditional methods of machining, the cut surface smears. This is a problem because it reduces the porosity of the material surface and will therefore affect the functionality (inhibit bone in growth). Hence, manufacturers use methods such as electrical discharge machining (EDM), a spark erosion process that does not mechanically impinge on the material surface. There are significant limitations of using EDM, mainly due to the geometry that can be created easily. In one method, an EDM electrode is a shaped tool that can only be used for a particular custom shape. Another method is to use wire EDM, but it has limited ability to create geometry, in particular concave surfaces, since the wire must be able to span the surface.

If machining can be used, then custom shapes can be created, simply based on the tool motion and cutting paths. A great advantage of this is that custom bone implants can be created based on a computed tomography (CT) scan, MRI scans, or other x-rays of the patient. As such, a bone implant could be created for each patient individually.

Therefore, what is needed is a process of cutting metallic foams that eliminates the problem of smeared surfaces and allows machining to be used.

BRIEF SUMMARY OF THE INVENTION

Therefore, it is an object of the present invention to improve over the state of the art.

It is a further object of the present invention to use an infiltrant material as a backing material to support the cellular structure of metallic foams.

It is another object of the present invention to use softer thermoplastics or waxes, which are subsequently frozen, often to near cryogenic temperatures for machining.

It is yet another object of the present invention to use epoxy materials that do not need to be frozen in order to support the foam structure.

It is also an object of the present invention to remove the infiltrant using melting if the material is a thermoplastic or wax material.

It is yet another object of the present invention to remove the infiltrant using burning in a furnace to remove thermoset materials such as epoxies.

It is an object of the present invention to eliminate the effect of smearing of metallic foams when they are cut using conventional machining methods such as milling or turning, sawing, grinding, planing, shaping, or filing.

It is another object of the present invention to avoid contamination of the metallic foam with any oils, coolants, chips, or other undesirable substances during the machining process by blocking the contaminants with the infiltrant material of this method.

One or more of these and/or other objects, feature, or advantages of the present invention will become apparent from the specification and claims that follow. No single embodiment needs to meet all of these objects.

According to one aspect of the present invention, a method of cutting metallic foams that eliminates the problem of smeared surfaces is provided. The method involves infiltration of the foam with another material to serve as a support structure to the foam when being cut. The method can be executed using softer polymeric materials such as waxes, which are then frozen for machining. These materials are subsequently heated and removed from the foam. In a similar manner, epoxy material can be used, which requires no freezing. In this method, the epoxy material is burnt from the foam upon completion of machining. The method allows for machining foams using conventional machining processes, rather than non traditional methods such as electrical discharge machining.

According to another aspect of the present invention, a method for customizing a bone implant for use in a patient is provided. The method includes infiltrating metallic foam with an infiltrant material to provide a support structure for the metallic foam, cutting the metallic foam to form a custom bone implant for the patient, and removing the infiltrant material from the metallic foam. The custom bone implant may be sized and shaped according to a CAD model associated with the patient, which may be constructed using data CT scan data or other types of medical imaging.

BRIEF DESCRIPTION OF THE DRAWINGS

The present invention will be better understood with reference to the appended drawing sheet, wherein:

FIG. 1A illustrates a smeared surface associated with conventional cutting while FIG. 1B illustrates metallic foam infiltrated with material, surface machined, and then infiltrant removed.

FIG. 2A provides an image of trabecular metal which is uncut. FIG. 2B provides an image of trabecular metal from conventional machining. FIG. 2C provides an image of trabecular metal after cutting with the methodology of the present invention.

DETAILED DESCRIPTION OF THE PREFERRED EMBODIMENT

The present invention relates to a process of cutting metallic foams through the use of an infiltrant material, which is subsequently removed after machining. The purpose of the infiltrant material is to act as a support structure for the cellular walls of the foam. As such, the infiltrant keeps the foam walls from bending/smearing during the cutting process. The method has been preliminarily tested using both wax and epoxy. When using wax, the foam is infiltrated by dipping into a vat of molten wax. Wax infiltrates the foam through a wicking action. During machining with softer materials like wax, the process involves freezing of the sample. This freezing can be done at any appropriately low temperature to maintain the hardness of the infiltrant. Tests have been performed with aerosol freezing sprays, however, freezing could be accomplished using other known cryogenic machining methods. One method would be to flow liquid nitrogen over the sample during machining. If an epoxy or other thermoset material is used, then the infiltration can occur at or near room temperature. As epoxies are generally harder, the method in this case does not necessarily involve freezing of the sample as the epoxies will generally retain hardness at elevated temperatures. Conventional coolants can be applied as needed when using epoxies.

Upon completion of the machining process, the infiltrant is removed. In the case of a softer material that can be melted, another heating process can be used to remove the material. For thermoset materials like epoxies, they can be removed via burning in a furnace. Tests with thermosets have been performed using an inert environment furnace to burn out the material. Subsequent to either process is an optional rinsing/soaking of the sample in a solvent to remove residue of the infiltrant.

Figure 1A:
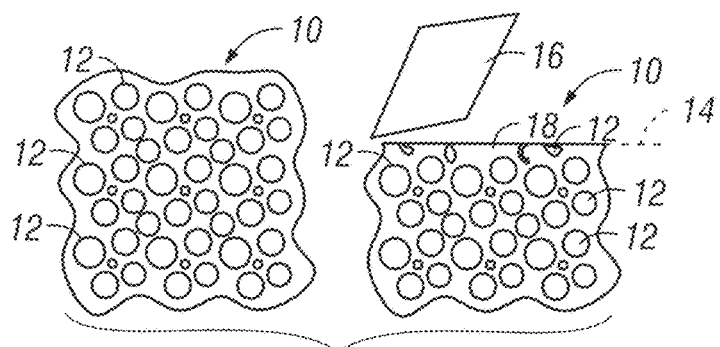
FIG. 1A to FIG. 1B compare the conventional cutting to the method of the present invention.
Figure 1B:
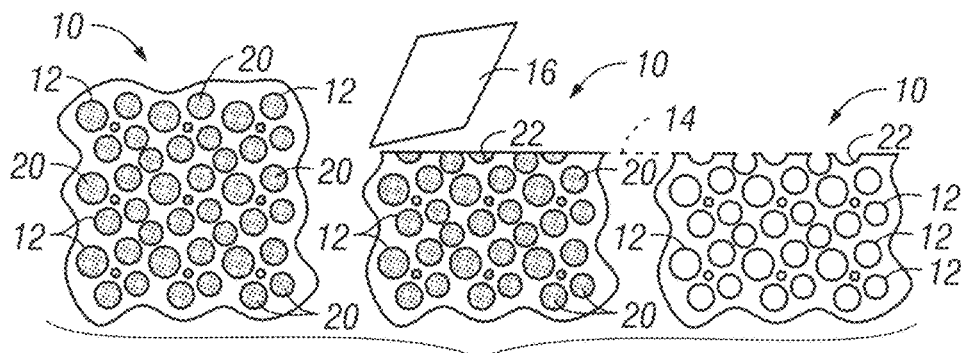
Figures 2A, 2B, 2C:
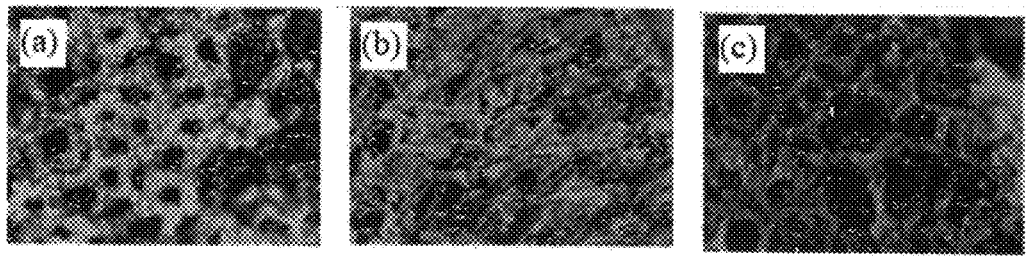
FIG. 2A to FIG. 2C provides microscope photos comparing a traditionally machined surface of Trabecular metal compared to the method of this invention. Samples were cut in the lab at Iowa State University.

FIG. 1A illustrates a traditional machining process where a foam 10 includes pores 12 throughout. When a machining tool 16 cuts the foam 10, such as along line 14, pores 12 along the surface 18 close. As illustrated in FIG. 1A, when a traditional machining approach is used, the surface of the material smears, causing the surface pores of the foam to close. Evidence of this is shown in the traditionally machined sample shown in FIG. 2B. FIG. 1B illustrates the use of the infiltrant, machining with infiltrant in place, and then subsequent removal of the infiltrant. The foam 10 is filled with an infiltrate 20 prior to machining. When a machining tool 16 cuts the foam 10, such as along line 14, the result is a surface 22 with pores 12 along the surface 22 not being closed. FIG. 2C shows an example of the same material cut using the method of this invention. In both cases, the sample is of Trabecular Metal (pure Tantalum metal foam). Both photos of machined surfaces (FIG. 2B, FIG. 2C) illustrate the exact same cutting parameters (½" Flat High Speed Steel end mill, 2 flutes, 500 RPM, 0.020" depth of cut and 10 inches per minute feed rate). The difference between FIG. 2B and FIG. 2C is the use of frozen wax infiltrant as the method of this invention, whereas FIG. 2B shows the surface smeared when machining without the frozen infiltrant. Similar results were achieved using an epoxy infiltrant.

Significantly, the present invention uses the infiltrant to support the cellular structure and the methodology involving infiltration, optional freezing, and then subsequent removal of the infiltrant. This method was based on a hypothesis that the smearing effect is a result of poor cutting, and likely bending of the cells walls during cutting. This invention results in the first known method to effectively cut metallic foams, in particular trabecular metal, through the use of a mechanical cutting process like machining.

Figures 3A, 3B:
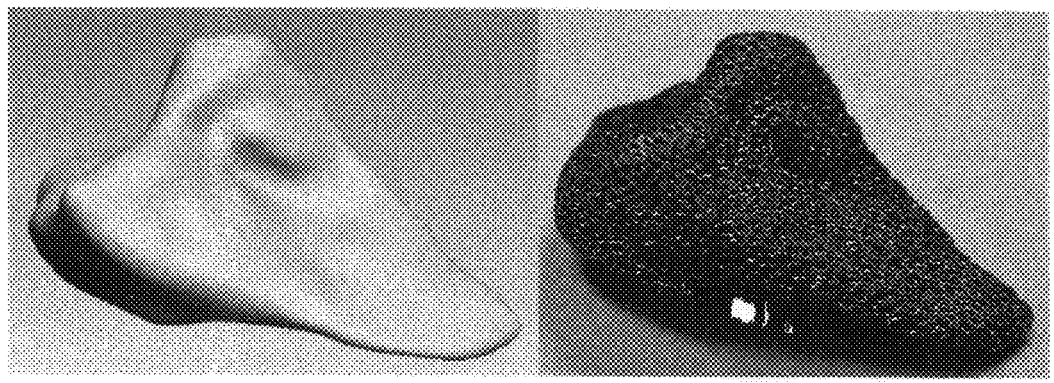
FIG. 3A illustrates a CAD model of a human femur fracture segment.
FIG. 3B illustrates a TM machined replica according to one method of the present invention.

The method of the present invention has been used in conjunction with a Rapid Machining process in the laboratory to illustrate its capabilities. As shown in FIGS. 3A-3B, a CAD model of a bone fragment (due to traumatic fracture) from a human Tibia was reverse engineered from CT scan data and replicated using CNC machining of Trabecular Metal.

The present invention allows for machining foams using conventional machining processes, rather than non-traditional methods such as electrical discharge machining (EDM). EDM is capable of cutting the material without smearing, but is not an easily customizable process. Moreover, recent research has shown that EDM has a detrimental effect on the material properties, in particular, a reduction in porosity. Initial testing of the process of the present invention indicates that the porosity of the Trabecular Metal may be preserved using this approach. This process can enable the creation of custom shaped TM implants of virtually any fee-form geometry, using a CT scan derived CAD model of the desired geometry.

Figure 4:
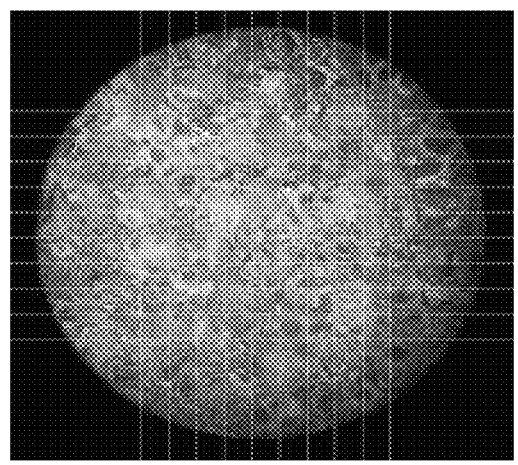
FIG. 4 illustrates a photographic image showing a reticle Grid imposed on 50×TM machined image (Grid space: 350 μm).

Several preliminary experiments have been conducted in order to quantify the effectiveness of the invented method at preserving TM surface porosity. In these studies, the surface porosity for fresh TM is assumed to be nominally 30% (fraction metal) with a range of ~20-40%. The pore size for TM ranges from around 400-700 µm. If the method for machining is perfect, one would expect similar porosity measure as in fresh TM; therefore, smearing is quantified herein using porosity measurements. In the experiments, a microscopic reticle analysis method was used, by overlaying a grid on the images of the cut surfaces. Maintaining focus on the surface of the cut TM, a grid point analysis using 0 or 1 was used to designate a void space or metal, respectively (FIG. 4).

For this investigation, two different machinable waxes were used with different hardness ratings ranging from Shore 50D to 52D. Each metal foam sample was submerged in molten wax within a vacuum chamber to remove bubbles, ensuring complete infiltration. Solidified samples of round TM rod were clamped in a simple collet chuck for machining. In each experiment, the sample was sprayed prior to and during machining using a freezing spray at −51° C. Other preliminary trials have also included liquid nitrogen spraying using a handheld spraying system.

Figure 5:
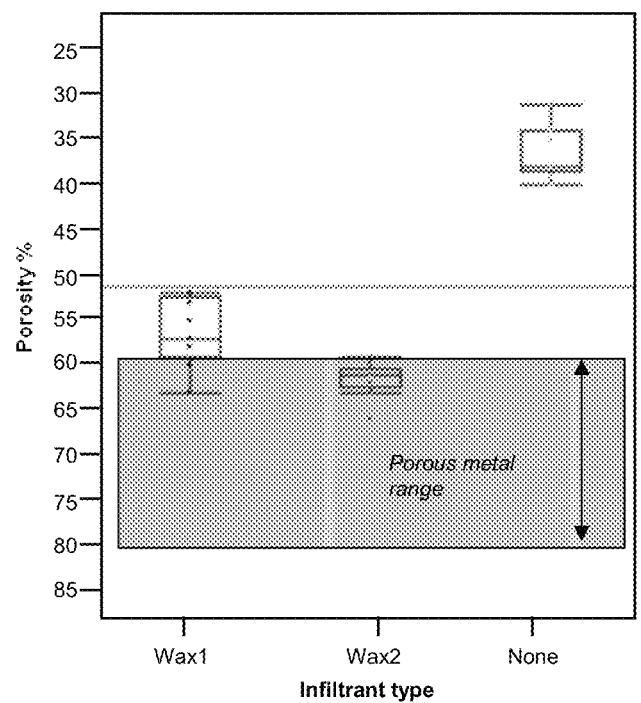
FIG. 5 is a box plot of surface porosity versus infiltrant method.

The material was machined using a ½" 4-flute HSS end mill at 10 ipm (254 mm/min) and 1000 rpm. The tests were replicated three times for both waxes and a dry (control) group at room temperature. Porosity results are illustrated using a box and whisker plot in FIG. 5. Each plot represents 9 porosity measurements across 3 replications at each material setup. This data illustrates the effect the invented method has on the resulting surface porosity. Overall, the two trials using the invented method perform significantly better than the control group. Although only the second wax trial falls within an expected range for TM, both cases represent a significant improvement over the smeared surfaces using conventional machining.

The present invention contemplates numerous options, variations, and alternatives. For example, the present invention contemplates variations in the infiltrant material, variations in the type of metallic foam, and variations in the specific machining processes performed. The present invention is not to be limited to the specific embodiments described herein.

What is claimed is:

1. A method of using metallic foam having a shape defined by a surface and a porosity throughout including the surface, comprising:
    infiltrating the metallic foam with an infiltrant material to provide a support structure for the metallic foam and thereby provide a modified metallic foam;
    mechanically machining along at least a portion of the surface of the modified metallic foam to reshape said modified metallic foam at the portion;
    removing the infiltrant material from the modified reshaped metallic foam; and
    exposing the reshaped portion in use;
    wherein the support structure provided by the infiltrant material deters smearing of the porosity at the surface of the portion of the reshaped metallic foam during mechanical machining;
    wherein the machining further comprises forming a bone implant from the metallic foam.

2. The method of claim 1 wherein the infiltrant material is a polymeric material.

3. The method of claim 2 further comprising freezing the infiltrant material.

4. The method of claim 3 wherein the step of removing the infiltrant material from the metallic foam comprises heating the infiltrant material.

5. The method of claim 1 wherein the metallic foam comprises trabecular metal.

6. The method of claim 1 wherein the mechanically machining further comprises customizing the bone implant for use in a patient.

7. The method of claim 6 wherein the customizing being performed using at least one of a computed tomography scan, a magnetic resonance imaging scan, and an x-ray of the patient.

8. The method of claim 6 further comprising implanting the bone implant in a patient.

9. The method of claim 1 wherein the infiltrant material comprises at least one of a thermoplastic, a wax, and an epoxy.

10. The method of claim 1 wherein the mechanically machining comprises at least one of milling, turning, sawing, grinding, planing, shaping, or filing.

11. A method for customizing a bone implant for use in a patient, the method comprising:
    infiltrating metallic foam with an infiltrant material to provide a support structure for the metallic foam and thereby provide a modified metallic foam;
    cutting the modified metallic foam to form a custom bone implant for the patient; and
    removing the infiltrant material from the modified metallic foam.

12. The method of claim 11 wherein the metallic foam comprises trabecular metal.

13. The method of claim 12 wherein the infiltrant material comprises wax.

14. The method of claim 12 wherein the infiltrant material comprises epoxy.

15. The method of claim 11 further comprising wherein the custom bone implant sized and shaped according to a CAD model associated with the patient.

16. The method of claim 15 wherein the CAD model is generated from at least one of a computed tomography scan of the patient, a magnetic resonance imaging scan of the patient, and an x-ray of the patient.

17. A method for customizing a bone implant for use in a patient, the method comprising:
    infiltrating metallic foam comprising trabecular metal with an infiltrant material comprising epoxy to provide a support structure for the metallic foam;
    cutting the metallic foam and the support structure to form a custom bone implant for the patient; and
    removing the infiltrant from the metallic foam.

* * * * *